United States Patent [19]

Tachibana

[11] Patent Number: 4,758,383
[45] Date of Patent: Jul. 19, 1988

[54] ERGOSTA-1,5,7,22-TETRAEN-3β-OL AND ITS USE AS AN INTERMEDIATE FOR 1α-HYDROXY VITAMIN $D_2$

[75] Inventor: Yoji Tachibana, Kawagoe, Japan

[73] Assignee: Nisshin Flour Milling Co., Ltd., Japan

[21] Appl. No.: 117,462

[22] Filed: Nov. 4, 1987

[30] Foreign Application Priority Data

Nov. 14, 1986 [JP] Japan .................................. 61-270951

[51] Int. Cl.$^4$ ............................................. C07J 9/00
[52] U.S. Cl. ................................................ 260/397.2
[58] Field of Search ..................................... 260/397.2

[56] References Cited

PUBLICATIONS

Chemical Abstracts; vol. 87 (1977) #118003c; Brynjolffssen et al.

Primary Examiner—Leonard Schenkman
Assistant Examiner—Joseph A. Lipovsky
Attorney, Agent, or Firm—Abelman Frayne Rezac & Schwab

[57] ABSTRACT

New processes for preparing new steroid derivatives including ergosta-1,5,7,22-tetraen-3β-ol, 1α-hydroxyergosteryl diacetate, etc. which are useful intermediates in the synthesis of 1α-hydroxy vitamin $D_2$. The processes include the new steps of reacting ergosta-1,4,6,22-tetraen-3-one with isopropenyl acetate in the presence of an acid catalyst followed by reduction to ergosta-1,5,7,22-tetraen-3β-ol. The overall yield leading to 1α-hydroxy vitamin $D_2$ is dramatically increased.

8 Claims, No Drawings

ERGOSTA-1,5,7,22-TETRAEN-3β-OL AND ITS USE AS AN INTERMEDIATE FOR 1α-HYDROXY VITAMIN D$_2$

FIELD OF THE INVENTION

This invention relates to new steroid derivatives which are useful intermediates in the preparation of 1α-hydroxy vitamin D$_2$, and also to a process of preparing the intermediates and 1α-hydroxy vitamin D$_2$.

BACKGROUND OF THE INVENTION

1α-Hydroxy vitamin D$_2$ exhibiting strong vitamin D activity is disclosed in U.S. Pat. No. 3,907,843. A synthetic route to 1α-hydroxy vitamin D$_2$ disclosed therein is shown in the following reaction scheme I, which includes conversion of isoergosterone (compound 1) prepared from ergosterol to ergosta-1,4,6,22-tetraen-3-one (compound 2) followed by reaction with hydrogen peroxide to give 1α,2α-epoxy-ergosta-4,6,22-trien-3-one (compound 3), reaction of this compound with liquid ammonia and metal lithium to give 1α-hydroxy-7,8-dihydroergosterol (compound 4) followed by acetylation to give 1α-acetoxy-7,8-dihydroergosteryl acetate (compound 5), dehydrogenation of this compound to 1α-hydroxyergosteryl diacetate (1α,3β-diacetoxy-ergosta-5,7,22-trien)(compound 6), irradiation of this compound with light, causing cleavage of the ring to give 1α,3β-diacetoxy previtamin D$_2$ (compound 7) and thermal isomerization and deacetylation of this compound to give 1α-hydroxy vitamin D$_2$ (compound 8). The synthesis of 1α-hydroxy vitamin D$_2$ by the above processes, however, gives rise to a number of problems. The reaction yield of the compounds is low including 16% yield in the formation of compound 5 from compound 3 and less than 10% yield in the formation of compound 6 from compound 5, and hence the overall yield through the synthesis of compound 6 from compound 1 amounts to less than 0.4%. In the conversion of compound 3 into compound 4, use of liquid ammonia and metal lithium is highly dangerous. In the conversion of compound 5 into compound 6, there is formed as by-products an isomeric compound 9 (1α,3β-diacetoxy ergosta-4,6,22-trien) which is difficult to separate and is responsible for reducing the purity of 1α-hydroxy vitamin D$_2$. In view of the foregoing problems, the prior processes are not satisfactory for the production of 1α-hydroxy vitamin D$_2$ in industrial scale.

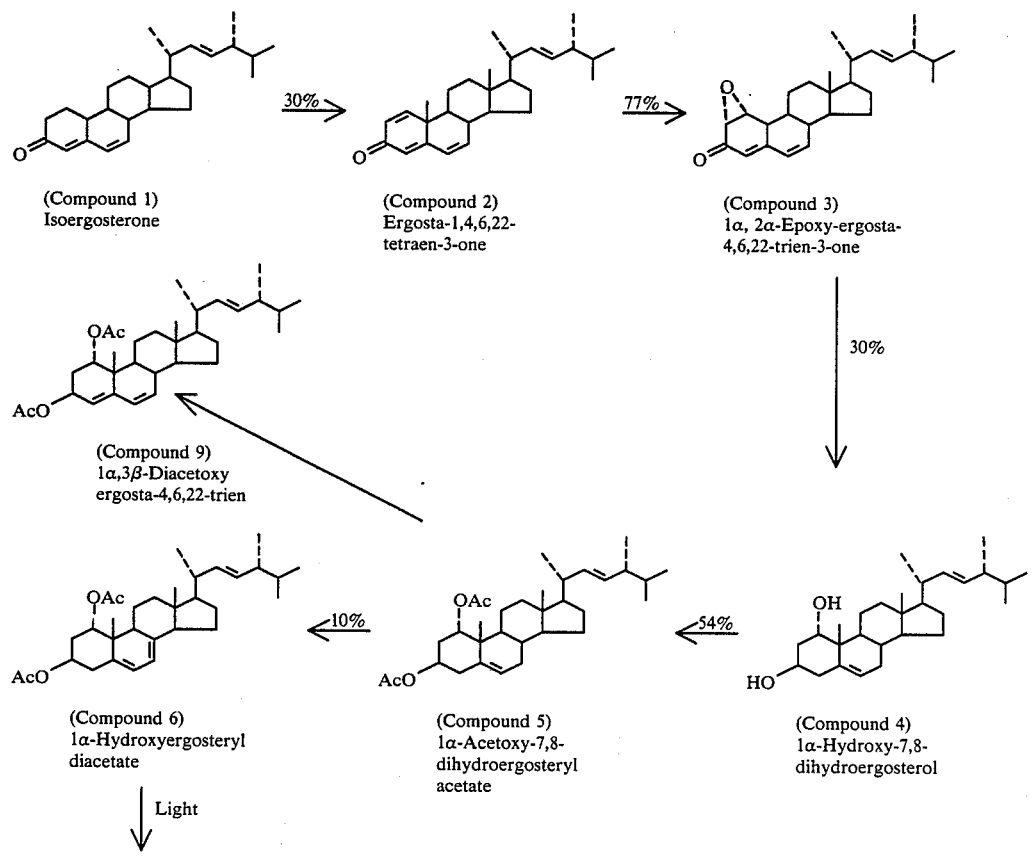

Reaction Scheme I

-continued
Reaction Scheme I

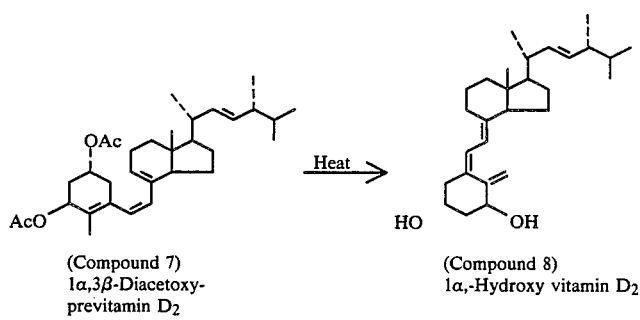

(Compound 7)
1α,3β-Diacetoxy-
previtamin D₂

(Compound 8)
1α,-Hydroxy vitamin D₂

By the overall reaction route described above, it is difficult to overcome the problems of low yield of the desired 1α-hydroxy vitamin $D_2$, difficulties in the reaction operation and low purity of the product. There is thus a need for a method for the synthesis of 1α-hydroxy ergosteryl diacetate (compound 6) in good yield according to a different reaction route from the prior art, said compound 6 leading to a previtamin $D_2$ by photoreaction.

Now, we have studied the prior art process for the preparation of 1α-hydroxyergosteryl diacetate starting from ergosta-1,4,6,22-tetraen-3-one and as a result it is found that a process via the intermediate, ergosta-1,5,7,22-tetraen-3β-ol can provide the desired compounds in more favorable yields, simpler reaction operation and higher purity of the product as compared with the above prior art processes.

SUMMARY OF THE INVENTION

An object of this invention is to provide a new intermediate compound, ergosta-1,5,7,22-tetraen-3β-ol and a process for the preparation thereof. Another object of the invention is to provide 1α-hydroxyergosteryl diacetate, the precursor for 1α-hydroxy vitamin $D_2$ by a process comprising the new steps via ergosta-1,5,7,22-tetraen-3β-ol. Further object of the invention is to provide a simpler process for the preparation of 1a-hydroxy vitamin $D_2$ in high yield.

Other objects, advantages and aspects of this invention will become apparent from the following description.

DETAILED DESCRIPTION OF THE INVENTION

The process of the invention is for example illustrated by the following reaction scheme II, including the synthesis of the new intermediate compound, ergosta-1,5,7,22-tetraen-3β-ol and that of 1α-hydroxyergosteryl diacetate via the said 3β-ol. As is apparent from the reaction scheme II, the intermediate products and the reaction route in the present invention are different from those shown in the reaction scheme I. In this situation, the compounds in the reaction scheme II are designated by using different numbers from those in the reaction scheme I. In the reaction scheme II, the starting material, ergosta-1,4,6,22-tetraen-3-one is designated by formula (II) (compound 2 in the reaction scheme I) and the percursor 1α-hydroxyergosteryl diacetate is designated by formula (X) (compound 6 in the reaction scheme I).

Reaction Scheme II

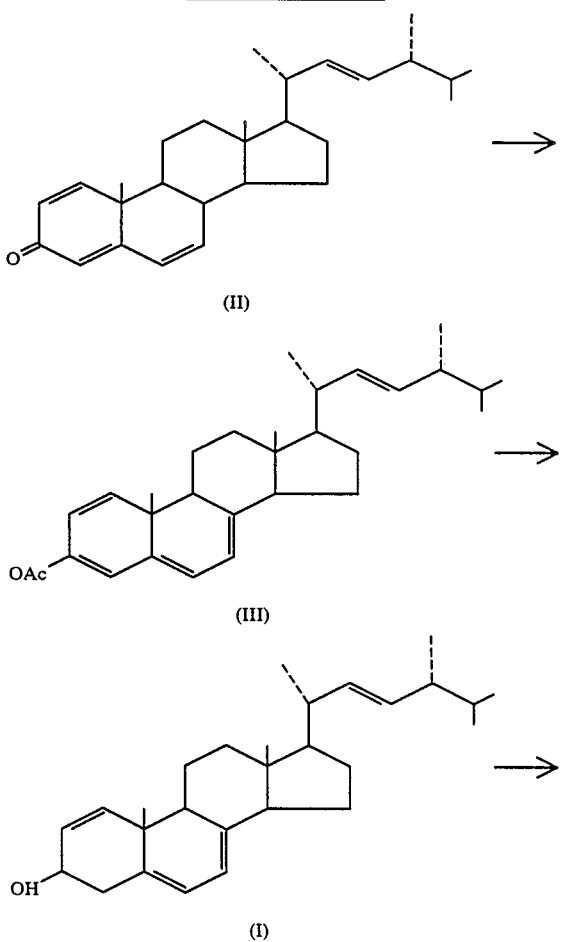

-continued
Reaction Scheme II
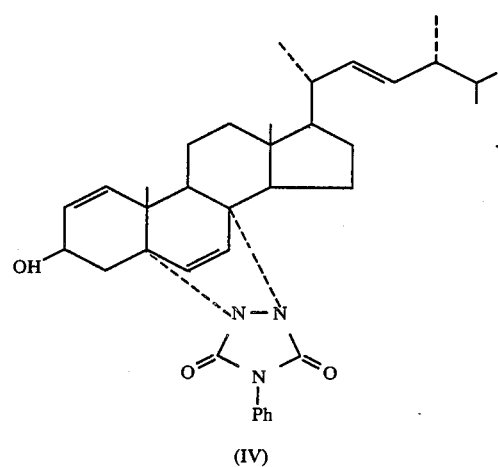
(IV)
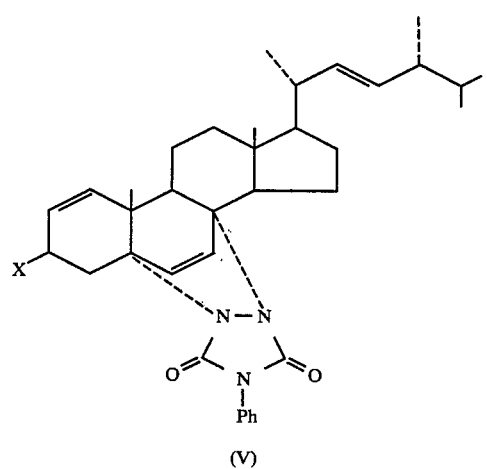
(V)
(X = protected hydroxyl group)
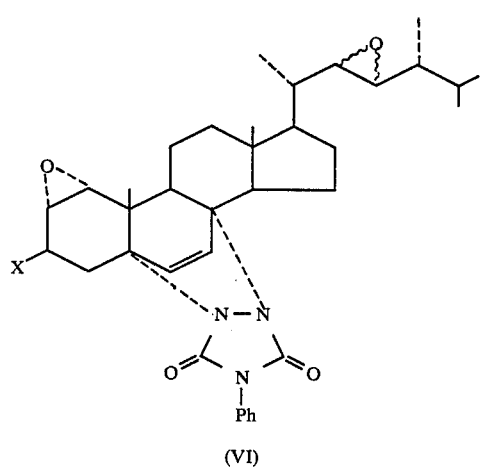
(VI)
-continued
Reaction Scheme II
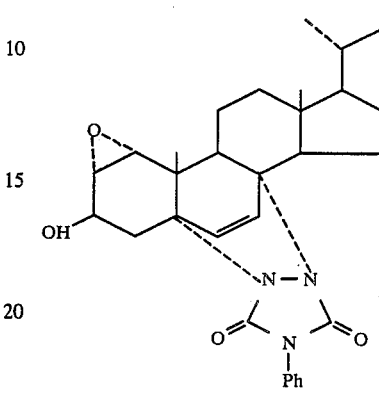
(VII)
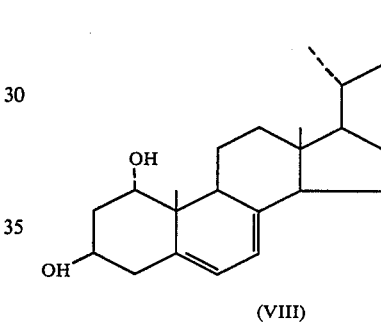
(VIII)
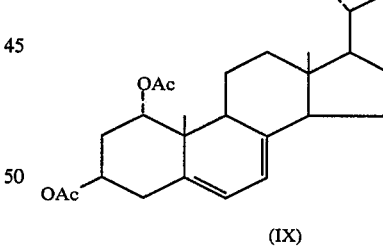
(IX)
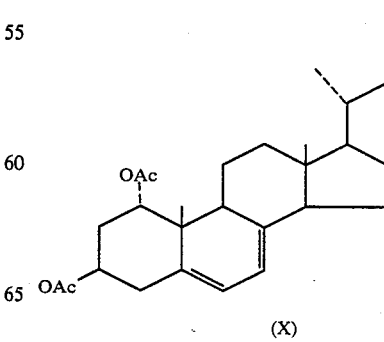
(X)

-continued
Reaction Scheme II

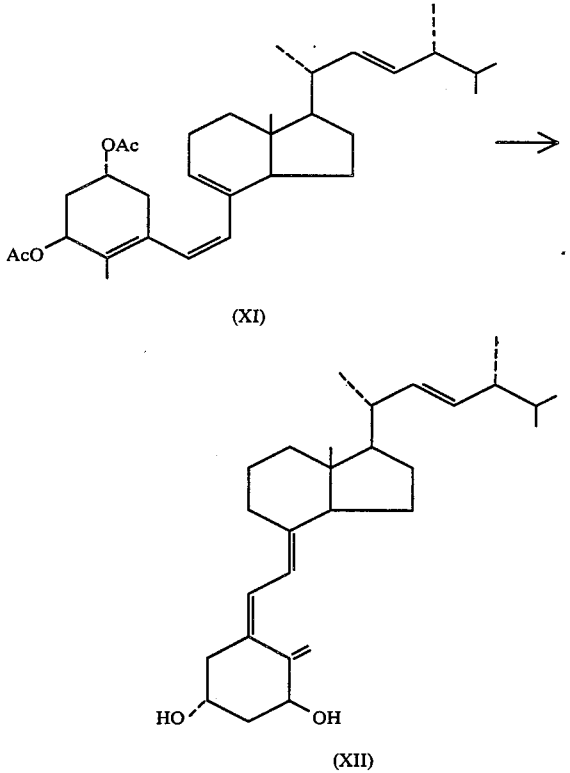

(XI)

(XII)

The process of the invention is particularly applicable to the preparation of the intermediate compounds including ergosta-1,5,7,22-tetraen-3β-ol of formula (I) and 1α-hydroxy erogostearyl diacetate of formula (X), the precursor for 1α-hydroxy vitamin D₂.

In the first step of the process, reaction of ergosta-1,4,6,22-tetraen-3-one of formula (II) with isopropenyl acetate leads to formation of ergosta-1,3,5,7,22-pentaen-3-yl-acetate of formula (III).

The reaction in the first step is preferably carried out in an organic solvent, e.g., a hydrocarbon solvent such as n-hexane, benzene and toluene, a ketone solvent such as acetone and methyl ethyl ketone and an ester solvent such as ethyl acetate and butyl acetate, at a temperature between ordinary temperature and a reflux temperature, preferably a temperature between 80° and 150° C. and in the presence of an acid catalyst. The acid catalysts used in the reaction include organic acids such as p-toluenesulfonic acid, methanesulfonic acid and the like and inorganic acids such as hydrochloric acid, sulfuric acid, acid potassium sulfate and the like. These acid catalysts are generally used in the range of 0.1 to 10 moles per mole of the compound of formula (II).

Isopropenyl acetate is used in the range of 1 to 100 moles and preferably 10 to 50 moles per mole of the compound of formula (II). If isopropenyl acetate is used in large excess, no additional solvent is required since isopropenyl acetate serves by itself as a reaction solvent.

In the second step, ergosta-1,3,5,7,22-pentaen-3-yl-acetate of formula (III) thus prepared is subjected to reduction to form ergosta-1,5,7,22-tetraen-3β-ol of formula (I). The reducing agents used in the reaction of this step include metal hydrides such as lithium aluminum-hydride (LiAlH₄), sodium borohydride (NaBH₄), calcium borohydride (Ca(BH₄)₂), zinc borohydride (Zn(BH₄)₂) and the like. Of these metal hydrides, Ca(BH₄)₂ is preferred. These metal hydrides are generally used in more excess amount than the theoretical amount. In general, 5 to 20 times the theoretical amount are used. The reduction is carried out in an organic solvent, e.g., ether and at a temperature between −20° C. and room temperature, preferably a temperature between −5° C. and 5° C.

The compound of formula (I), ergosta-1,5,7,22-tetraen-3β-ol thus prepared is reacted with 4-phenyl-1,2,4-triazoline-3,5-dione to yield the compound of formula (IV) which is a Diels-Alder adduct. The reaction is carried out at a temperature between 0° C. and room temperature in the presence of a conventional organic solvent, e.g., a hydrocarbon solvent such as n-hexane, benzene and toluene, a ketone solvent such as acetone and methyl ethyl ketone and an ester solvent such as ethyl acetate and butyl acetate. 4-Phenyl-1,2,4-triazoline-3,5-dione is used in the amount of 1.0 to 1.5 moles per mole of the compound of formula (I).

The Diels-Alder adduct, the compound of formula (IV) is converted to the compound of formula (V) by protecting a hydroxyl group at the 3-position of the compound (IV), e.g., with an eliminable protecting group. Suitable protecting groups are sterically bulky groups which are easily eliminable under mild conditions. The compounds for introduction of the protecting group include silyl compounds, e.g., t-butyldimethylsilyl chloride. In addition, t-butyldiphenylsilyl chloride can be taken into consideration. In the introduction of the protecting group, the reaction is preferably caused to proceed in the presence of a base as an acid binding agent, e.g., imidazole, triethylamine and diethylcyclohexylamine.

The compound of formula (V) having the protected hydroxyl group at the 3-position is converted to the compound of formula (VI) by epoxidizing the 1,2-double bond and the 22,23-double bond in the compound (V). For the epoxidation, the reagent is used including a variety of peracids or mixtures of organic acids and hydrogen peroxide. Preferred reagents include perbenzoic acid, m-chloroperbenzoic acid and the like. The epoxidation is carried out at a temperature between 0° C. and room temperature using the reagent in the amount of 1.5 to 5.0 times the theoretical amount for the compound of formula (V).

The epoxidized compound of formula (VI) is then subjected to the reaction for removal of the protecting group at the 3-position. This reaction is carried out e.g., using a solution of tetrabutylammonium fluoride in tetrahydrofuran. Likewise, CH₃COOH/H₂O can be used. The reaction temperature is in the range between 0° C. and room temperature.

The compound of formula (VII) having a free hydroxyl group at the 3-position is converted to the compound of formula (VIII) by subjecting to reduction. This reduction employs the conditions similar to those used in reduction of the compound (III) to the compound (I). Lithium aluminum hydride is especially preferred for the reducing agents used herein.

The reduced product, i.e., the compound of formula (VIII) is then converted to the diacetylated product of formula (IX) by acetylation. The acetylation can be carried out using known acetylating agents, e.g., pyridine/acetic anhydride or acetyl chloride/pyridine.

The diacetylated product, the compound of formula (IX) thus prepared is treated with an alkali metal iodide, e.g., sodium iodide in the presence of a suitable solvent such as trifluoroacetic anhydride, thereby converting the epoxy group at the 22,23-position to the ethylene group, leading to the formation of 1α-hydroxy ergosteryl diacetate of formula (X). In this reaction, the alkali metal iodide is used in the amount of 5 to 40 times that of the compound of formula (IX). The reaction temperature is in the range between 0° and 40° C.

The compound of formula (X) prepared in accordance with the process of the present invention is subjected to irradiation with light in the usual way, thereby leading to the cleavage of the steroid ring to form 1α,3β-diacetoxy previtamin $D_2$ (the compound of formula (XI)), followed by thermal isomerisation and de-acetylation according to a conventional method to produce the desired 1α-hydroxy vitamin $D_2$, i.e., the compound of formula (XII).

It will thus be apparent that the steroids including the compounds of formulas (I), (IV), (V), (VI), (VII), (VIII), (IX) and (X) prepared in accordance with the present invention are valuable intermediates in the synthesis of a wide range of biologically useful materials, particularly 1α-hydroxy vitamin D derivatives and related compounds.

According to the process of the present invention using the reaction route and intermediates different from the prior art process, the following advantages are achieved. The desired 1α-hydroxy-ergosteryl diacetate can be produced in much better yield than the prior art process, the overall yield in the present invention starting from the compound of formula (II) amounting to approximately 11.1%, whereas the overall yield in the prior art starting from compound 2 being only 1.2%. Accordingly, the overall yield leading to 1α-hydroxy vitamin $D_2$ amounts to as high as 1.9% according to the process of the present invention, in comparison with 0.20% according to the prior art process. Further, the reaction reagents used in the present invention are easy to handle, e.g., because of their safety and the desired products are of high purities, as compared with those of the prior art. Thus, the processes of the present invention are of great significance in industrial production of the vitamin $D_2$.

1α-Hydroxy vitamin $D_2$ is less toxic than 1α-hydroxy vitamin $D_3$ in the rat as disclosed in "Proceedings of the Society for Experimental Biology and Medicine 178, 432-436 (1985)". An $LD_{50}$ of 0.2 mg/kg body weight has been determined for 1α-hydroxy vitamin $D_2$ in the rat. In comparison, the $LD_{50}$ for 1α-hydroxy vitamin $D_2$ is between 3.5 and 6.5 mg/kg.

The invention is further illustrated by the following examples.

EXAMPLE 1

Preparation of ergosta-1,3,5,7,22-pentaen-3-yl-acetate (III)

Ergosta-1,4,6,22-tetraen-3-one (II) (10.0 g), p-toluene sulfonic acid (10.0 g) and isopropenyl acetate (100 ml) were added to butyl acetate (100 ml). After heating under reflux for 16 hours, a reaction solution was washed with water until it was neutral, dried over sodium sulfate ($Na_2SO_4$) and thereafter the solvent was distilled off. Crystallization of the residue from acetone gave 7.6 g (69% yield) of ergosta-1,3,5,7,22-pentaen-3-yl-acetate (III), m.p. 154°-156° C.

UV: λmax (ethanol) 252 nm ($\epsilon$=9,200).

mass spectrum: m/e 434($M^+$).

NMR(δ, $CDCl_3$): 5.64-5.98(m,5H), 5.21(m,2H, H-22,H-23), 2.20(s,3H,$COCH_3$).

EXAMPLE 2

Preparation of ergosta-1,5,7,22-tetraen-3β-ol (I)

Calcium chloride (15.0 g) was dissolved in methanol (150 ml) and cooled to −10° C. To a cooled solution was added dropwise while keeping at −10° C. a solution of sodium borohydride (7.5 g) in ethyl alcohol (150 ml) and the solution was stirred at the same temperature for 30 minutes. A solution of ergosta-1,3,5,7,22-pentaen-3-ylacetate (III) (5.0 g) from Example 1 in diethyl ether (100 ml) was added dropwise at a temperature between −5° and −10° C. The reaction mixture was stirred at a temperature between 0° and −5° C. for 3 hrs. and then at room temperature for 3 hrs. 50% Acetic acid was added to prepare a uniform solution and the solution was extracted with ethyl acetate. The extract was washed with water, then an aqueous sodium bicarbonate solution and dried. Ethyl acetate was concentrated and the residue was purified by silica gel chromatography (eluted with chloroform) followed by crystallization with acetone to give 4.2 g (90% yield) of ergosta-1,5,7,22-tetraen-3β-ol (I), m.p. 156°-157° C.

UV: λmax 282 nm($\epsilon$=11,000).

mass spectrum: m/e 394($M^+$).

NMR(δ, $CDCl_3$): 5.47-5.78(m,4H), 5.21(m,2H, H-22,H-23), 4.31(1H,m,H-3).

EXAMPLE 3

Preparation of Diels-Alder adduct (IV)

The ergosta-1,5,7,22-tetraen-3β-ol (I) (3.2 g) from Example 2 was dissolved in ethyl acetate (30 ml) and 4-phenyl-1,2,4-triazoline-3,5-dione (1.6 g) was added by drops. The solvent was distilled off and the residue was purified by silica gel chromatography (eluted with chloroform), yield 4.2 g (90%), m.p. 169°-170° C. (after crystallization with methanol).

$^1$H NMR δ($CDCl_3$): 7.40(5H,m ,$C_6H_5$), 6.36(2H, q,H-6,H-7), 6.04(2H,m,H-1,H-2), 5.20(2H,m,H-22,H-23), 5.06(1H, m,H-3).

Calc.for $C_{36}H_{47}N_3O_3$: C 75.87%; H 8.33%; N 7.37%; Found: C 75.74%; H 8.34%; N 7.29%.

EXAMPLE 4

Preparation of the silyl derivative (V) of the Diels-Alder adduct

The Diels-Alder adduct (IV) (1.4 g) from Example was dissolved in dimethylformamide (3.0 ml). To a solution was added imidazole (0.6 g) and t-butyldimethylsilyl chloride (0.6 g), the solution was warmed to 40° C. and kept at this temperature for 30 minutes. The reaction mixture was extracted with ether, washed with water, dried over $Na_2SO_4$ and the ether was distilled off. Crystallization of the residue from methanol-ether gave the title compound, m.p. 186°-188° C., yield 1.5 g(90%).

$^1$H NMR δ($CDCl_3$): 7.40(5H,m,$C_6H_5$), 6.37(2H, q, H-6,H-7), 5.69(2H,m,H-1,H-2), 5.18(2H,m,H-22,H-23), 4.99 (1H,m,H-3).

Calc. for $C_{42}H_{61}N_3O_3Si$: C 73.73%; H 9.01%; N 6.14%; Found: C 73.71%; H 9.08%; N 6.15%.

EXAMPLE 5

Preparation of 1,2-and 22,23-diepoxide (VI)

The silyl derivative (V) (1.5 g) from Example 4 was dissolved in chloroform (50 ml), m-chloroperbenzoic acid (1.5 g) was added to a solution and the mixture was reacted at room temperature for 24 hrs. The reaction solution was washed with 10% aqueous solution of potassium carbonate, then water, dried over $Na_2SO_4$ and crystallized with methanol to give the title compound, m.p. 194°–195° C., yield 1.4 g(90%).

$^1$H NMR $\delta$(CDCl$_3$): 7.32(5H,m,C$_6$H$_5$), 6.19(2H,q, H-6,H-7), 4.81(1H m,H-3).

Calc. for $C_{42}H_{61}N_3O_5Si$: C 70.43%; H 8.60%; N 5.87%; Found: C 70.34%; H 8.61%; N 5.85%.

EXAMPLE 6

Preparation of 1,3-diol (VIII)

To a solution of the diepoxide (VI) (1.4 g) from Example 5 in tetrahydrofuran (10 ml) was added at a temperature between 0° and 5° C. a 1M tetrahydrofuran solution of tetrabutylammonium fluoride (3 ml). The mixture was reacted at the same temperature for 18 hrs, extracted with ethyl acetate, washed with water, dried over $Na_2SO_4$ and the solvent was distilled off. The residue was purified by silica gel chromatography (eluted with chloroform). The distillate (VII, 0.9 g) (79% yield) was dissolved in tetrahydrofuran (20 ml), added dropwise to a tetrahydrofuran solution (40 ml) of lithium aluminum hydride (2.0 g) and refluxed for 1.5 hrs. Excess lithium aluminum hydride was decomposed with water and adjusted to pH 1–2 with diluted hydrochloric acid.

The reaction mixture was extracted with ethyl acetate, washed with water and dried over $Na_2SO_4$. The solvent was distilled off and the residue was purified by silica gel chromatography (eluted with 4/1 chloroform-/ethyl acetate) to give the title compound, yield 0.4 g (62%), m.p. 157°–158° C. (after crystallization from acetone).

$^1$H NMR $\delta$(CDCl$_3$): 5.70, 5.38(2H,m,H-6,H-7), 4.05(1H,m,H-3), 3.73(1H,bs,H-1).

Calc. for $C_{28}H_{44}O_3$: C 78.44%; H 10.37%; Found: C 77.16%; H 10.01%.

EXAMPLE 7

Preparation of 1α,3β-diacetoxy-ergosta-5,7,22-trien (X)

The diol (VIII) (0.6 g) from Example 6 was charged with pyridine (2 ml) and acetic anhydride (2 ml) and reacted at a temperature between 80° and 85° C. for 1 hr. The reaction product was extracted with hexane, washed with sodium bicarbonate solution, then water and dried over $Na_2SO_4$. The solvent was distilled off to give 0.7 g of the compound (IX). Sodium iodide (3.5 g) was dissolved in tetrahydrofuran/acetonitrile (1/1, 30 ml), to which trifluoroacetic anhydride (1 ml) was added. A solution of the compound (IX) (0.7 g) in tetrahydrofuran/acetonitrile (1/1, 10 ml) was added dropwise at a temperature between 0° and 5° C. and kept at the same temperature for 40 hrs. After completion of the reaction, the reaction mixture was extracted with hexane, washed with 5% aqueous sodium bisulfite solution, then water and dried over $Na_2SO_4$. Distilling off hexane, purification of the residue by silica gel chromatography (eluted with 95/5 hexane/ethyl acetate) and crystallization of the distillate from ethanol gave the title compound, yield 0.33 g (50%), m.p. 128°–130° C.

$^1$H NMR $\delta$(CDCl$_3$): 5.68, 5.40(2H,m,H-6,H-7), 5.19(2H,m,H-22,H-23), 5.01(2H,m, H-1,H-3), 2.08, 2.03(6H,s,COCH$_3$).

Calc. for $C_{32}H_{48}O_4$: C 77.36%; H 9.76%; Found: C 77.14%; H 9.78%.

EXAMPLE 8

Preparation of 1α-hydroxy vitamin D$_2$ (XII)

1α,3β-Diacetoxy-ergosta-5,7,22-trien (X) (200 mg) from Example 7 was dissolved in ether (400 ml) and the solution was irradiated with high pressure mercury lamp (UM-452, Ushio Electric Co., Ltd.) for 10 minutes. After distilling off ether under reduced pressure, ethanol (50 ml) was added and the mixture was heated under reflux for 1 hr. Subsequently, a solution of potassium hydroxide (1 g) in ethanol (10 ml) was added and further heated under reflux for 10 minutes. The whole reaction was carried out in a nitrogen stream. After cooling, the reaction product was extracted with ether (200 ml). The extract was washed with water, dried over $Na_2SO_4$ and ether was distilled off under reduced pressure. Chromatography on silica gel of the residue (eluted with 95/5 chloroform/ethyl acetate) gave 55 mg of a crude 1α-hydroxy vitamin D$_2$ (XI). Crystallization of the crude vitamin from hexane/acetone gave 35 mg (17.5% yield) of a pure 1α-hydroxy vitamin D$_2$ (XI) as crystals, m.p. 146°–147° C., λ max 265 nm ($\epsilon$=18500, ethanol), $[\alpha]_D^{20}$+47° (c=0.25, ethanol).

What is claimed is:

1. Ergosta-1,5,7,22-tetraen-3β-ol of formula (I)

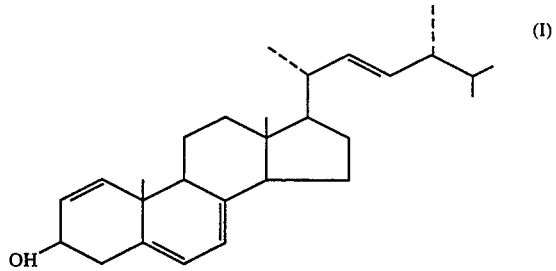

2. A process of preparing ergosta-1,5,7,22-tetraen-3β-ol of claim 1 which comprises reacting ergosta-1,4,6,22-tetraen-3-one of formula (II)

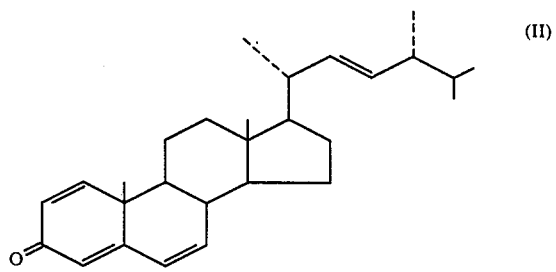

with isopropenyl acetate of the formula

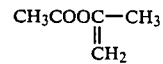

in the presence of an acid catalyst to form ergosta-1,3,5,7,22-pentaen-3-yl-acetate of formula (III)

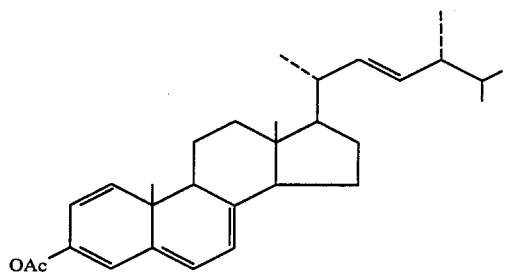

(III)

and reducing said acetate.

3. The process of claim 2 wherein the acid catalyst is paratoluenesulfonic acid, methanesulfonic acid, hydrochloric acid, sulfuric acid or potassium acid sulphate.

4. The process of claim 2 wherein the acid catalyst is used in the range of from 0.1 to 10 moles per mole of ergosta-1,4,6,22-tetraen-3-one.

5. The process of claim 2 wherein isopropenyl acetate is used in the range of from 1 to 100 moles per mole of ergosta-1,4,6,22-tetraen-3-one.

6. The process of claim 2 wherein ergosta-1,4,6,22-tetraen-3-one is reacted with the isopropenyl acetate in an organic solvent.

7. The process of claim 2 wherein the reduction is carried out at a temperature between −20° C. and room temperature in an organic solvent.

8. A process of preparing 1α-hydroxy vitamin D$_2$ of formula (XII)

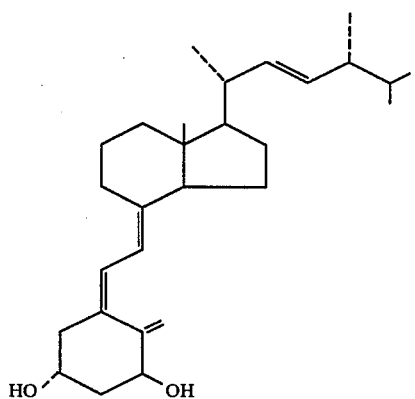

(XII)

which comprises the steps of: reacting ergosta-1,4,6,22-tetraen-3-one of formula (II)

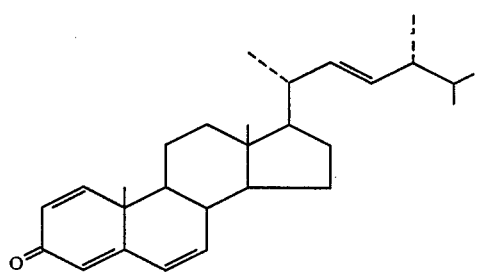

(II)

with isopropenyl acetate in the presence of an acid catalyst to form ergosta-1,3,5,7,22-pentaen-3-yl-acetate of formula (III)

(III)

reducing said acetate compound to form ergosta-1,5,7,22-tetraen-3β-ol of formula (I), (I)

reacting said 3β-ol compound with 4-phenyl-1,2,4-triazoline-3,5-dione to form a Diels-Alder adduct of formula (IV), (IV)

introducing a protecting group into a hydroxyl group at the 3-position of said Diels-Alder adduct to form a compound having a protected 3-hydroxyl group of formula (V),

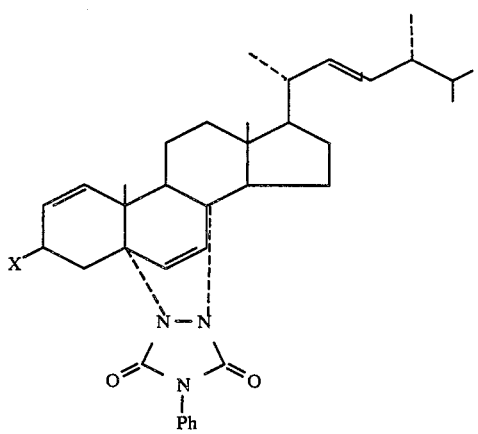

(V)

in which X represents a protected hydroxyl group, epoxidizing the 1,2- and 22,23-double bonds in said compound of formula (V) to form the epoxidized compound of formula (VI),

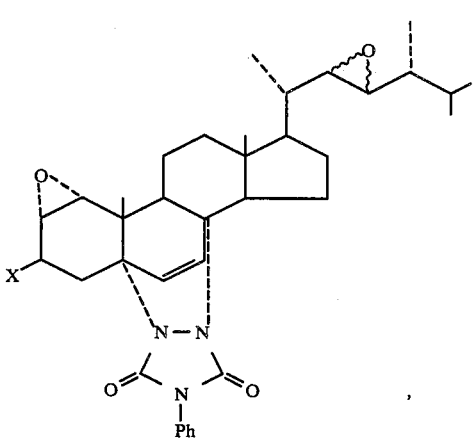

(VI)

subjecting said epoxidized compound to a reaction for removing the protecting group at the 3-position to form a compound having a free 3-hydroxyl group of formula (VII)

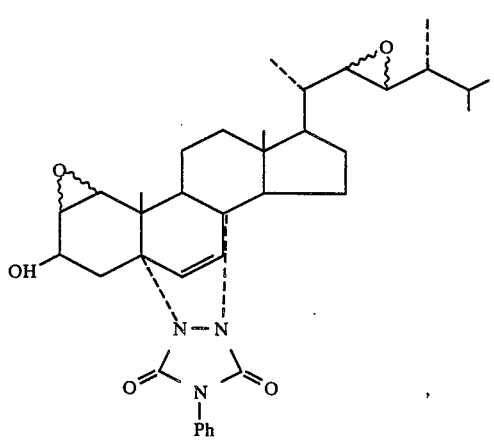

(VII)

reducing said compound of formula (VII) to form a 1,3-diol compound of formula (VIII),

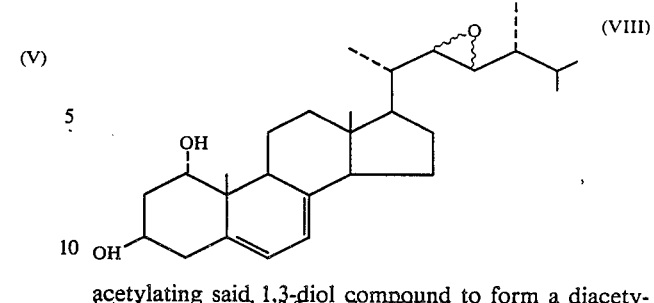

(VIII)

acetylating said 1,3-diol compound to form a diacetylated compound of formula (IX),

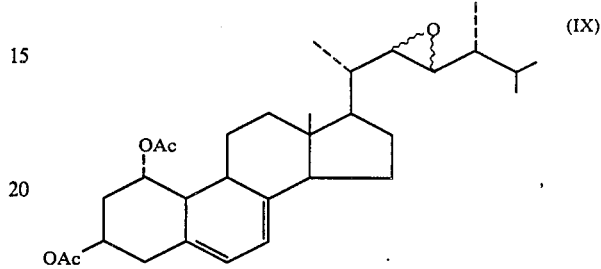

(IX)

treating said diacetylated compound with an alkali metal iodide to form 1α-hydroxyergosteryl diacetate of formula (X),

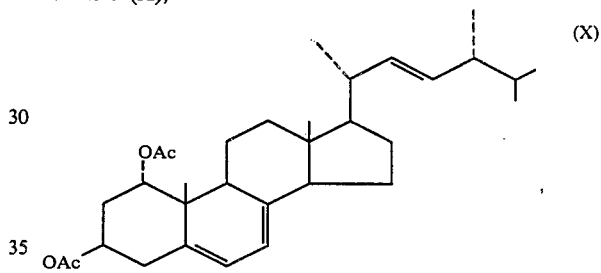

(X)

irradiating said diacetate with light to form 1α,3β-diacetoxy previtamin $D_2$ of formula (XI),

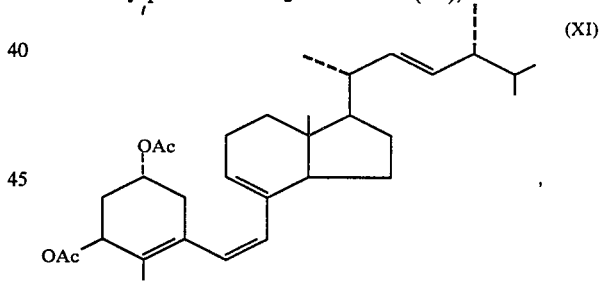

(XI)

and subjecting said previtamin $D_2$ to thermal isomerization and deacetylation to form 1α-hydroxy vitamin $D_2$ of formula (XII)

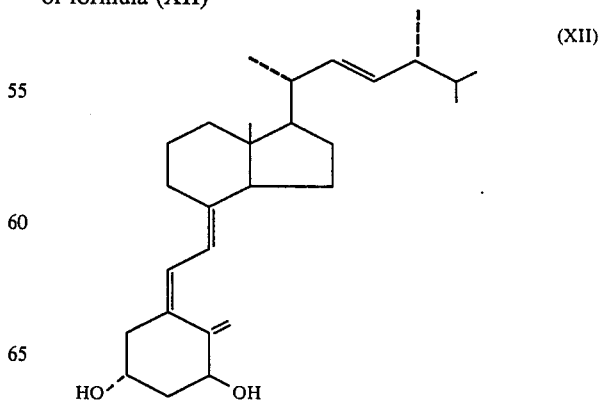

(XII)

* * * * *